(12) United States Patent
Hinchliffe

(10) Patent No.: US 6,589,240 B2
(45) Date of Patent: Jul. 8, 2003

(54) TISSUE BIOPSY APPARATUS WITH COLLAPSIBLE CUTTER

(75) Inventor: Peter W. J. Hinchliffe, Downington, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

(21) Appl. No.: 09/940,951

(22) Filed: Aug. 28, 2001

(65) Prior Publication Data

US 2003/0045873 A1 Mar. 6, 2003

(51) Int. Cl.[7] .............................................. A61B 18/14
(52) U.S. Cl. ........................... 606/47; 606/46; 600/566; 600/567
(58) Field of Search ........................... 606/47, 45, 46; 600/564–567

(56) References Cited

U.S. PATENT DOCUMENTS

| | | | |
|---|---|---|---|
| 5,085,658 A | | 2/1992 | Meyer |
| 5,085,659 A | | 2/1992 | Rydell |
| 5,133,360 A | * | 7/1992 | Spears .................. 600/567 |
| 5,217,458 A | | 6/1993 | Parins |
| 5,403,311 A | | 4/1995 | Abele et al. |
| 5,441,503 A | * | 8/1995 | Considine et al. ............ 606/46 |
| 5,456,689 A | | 10/1995 | Kresch et al. |
| 5,527,331 A | | 6/1996 | Kresch et al. |
| 5,578,030 A | | 11/1996 | Levin |
| 5,643,197 A | | 7/1997 | Brucker et al. |
| 5,807,395 A | | 9/1998 | Mulier et al. |
| 5,810,806 A | * | 9/1998 | Ritchart et al. ............... 606/45 |
| 5,913,857 A | | 6/1999 | Ritchart et al. |
| 5,928,163 A | | 7/1999 | Roberts et al. |
| 5,944,716 A | | 8/1999 | Hektner |
| 5,957,863 A | * | 9/1999 | Koblish et al. .............. 600/567 |
| 5,957,921 A | | 9/1999 | Mirhashemi et al. |
| 5,980,545 A | | 11/1999 | Pacala et al. |
| 6,036,698 A | * | 3/2000 | Fawzi et al. ................. 600/562 |
| 6,123,084 A | | 9/2000 | Jandak et al. |
| 6,136,014 A | | 10/2000 | Sirimanne et al. |
| 6,162,216 A | | 12/2000 | Guziak et al. |
| 6,176,856 B1 | | 1/2001 | Jandak et al. |
| 6,200,313 B1 | | 3/2001 | Abe et al. |
| 6,214,024 B1 | | 4/2001 | Houser |
| 6,221,029 B1 | | 4/2001 | Mathis et al. |
| 6,228,058 B1 | * | 5/2001 | Dennis et al. ............ 604/164.01 |
| 6,261,241 B1 | | 7/2001 | Burbank et al. |
| 6,277,083 B1 | | 8/2001 | Eggers et al. |
| 6,287,304 B1 | | 9/2001 | Eggers et al. |
| 6,454,727 B1 | | 9/2002 | Burbank et al. |

FOREIGN PATENT DOCUMENTS

| | | |
|---|---|---|
| DE | 3632197 | 3/1988 |
| WO | WO 9003152 | 4/1990 |
| WO | WO 9944506 | 9/1999 |
| WO | WO 0012009 | 3/2000 |
| WO | WO 0030531 | 6/2000 |

* cited by examiner

Primary Examiner—Lee Cohen
(74) Attorney, Agent, or Firm—Neil D Gershon

(57) ABSTRACT

A surgical apparatus for removing a portion of tissue comprising an elongated body having a distal edge, a collapsible cutting member mounted to the elongated body, having an opening therethrough and extending distally of the distal edge of the elongated body. The cutting member has a closed loop conductive surface and is movable from a first loop configuration to a second smaller loop configuration, the exposed conductive distal edge forming an electrosurgical cutting surface for applying electrical energy to tissue. The cutting member resects a tubular region of tissue as the apparatus is advanced through tissue and the resected tissue extends through an opening in the cutting ring for containment within the elongated body.

21 Claims, 10 Drawing Sheets

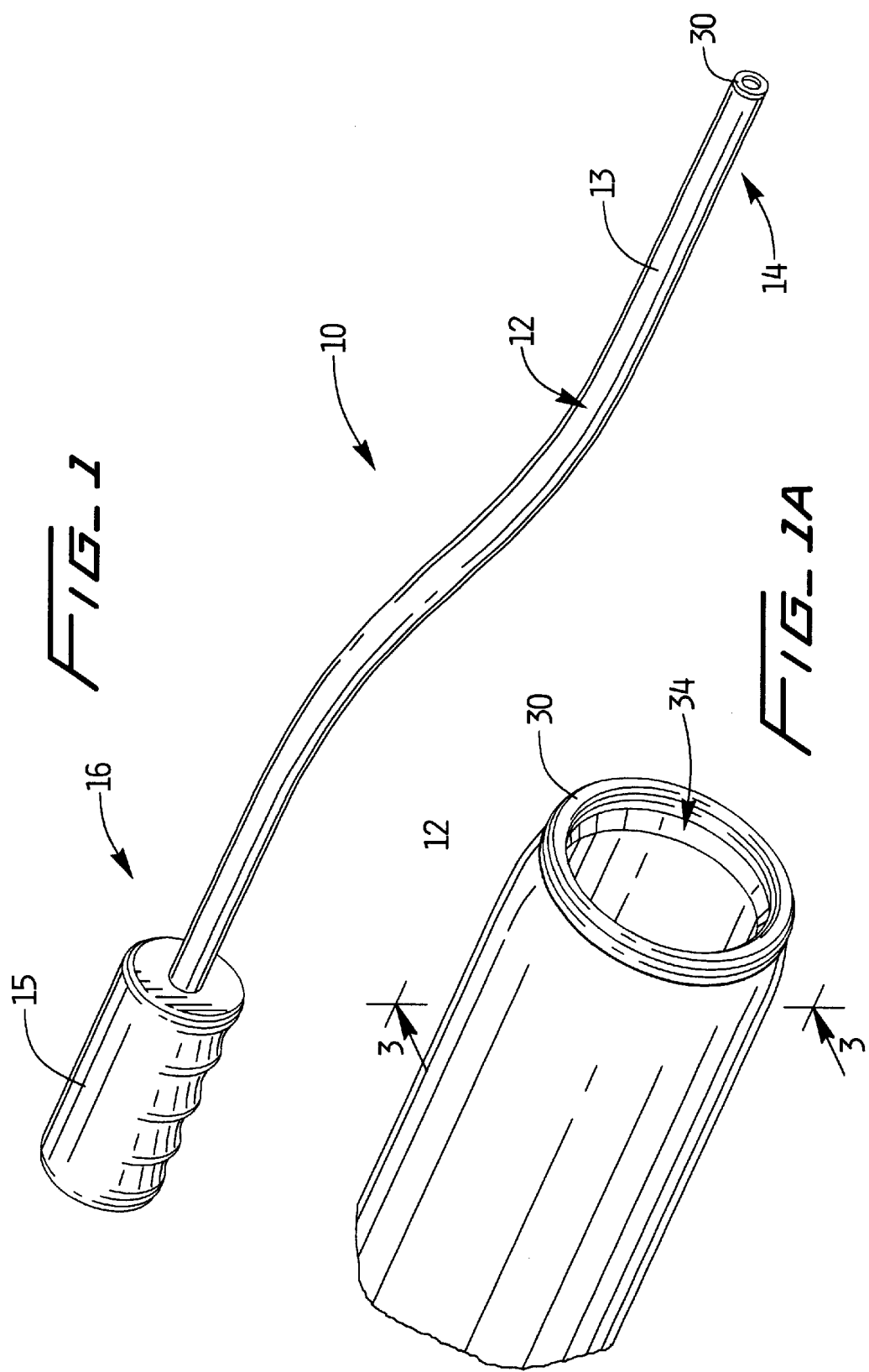

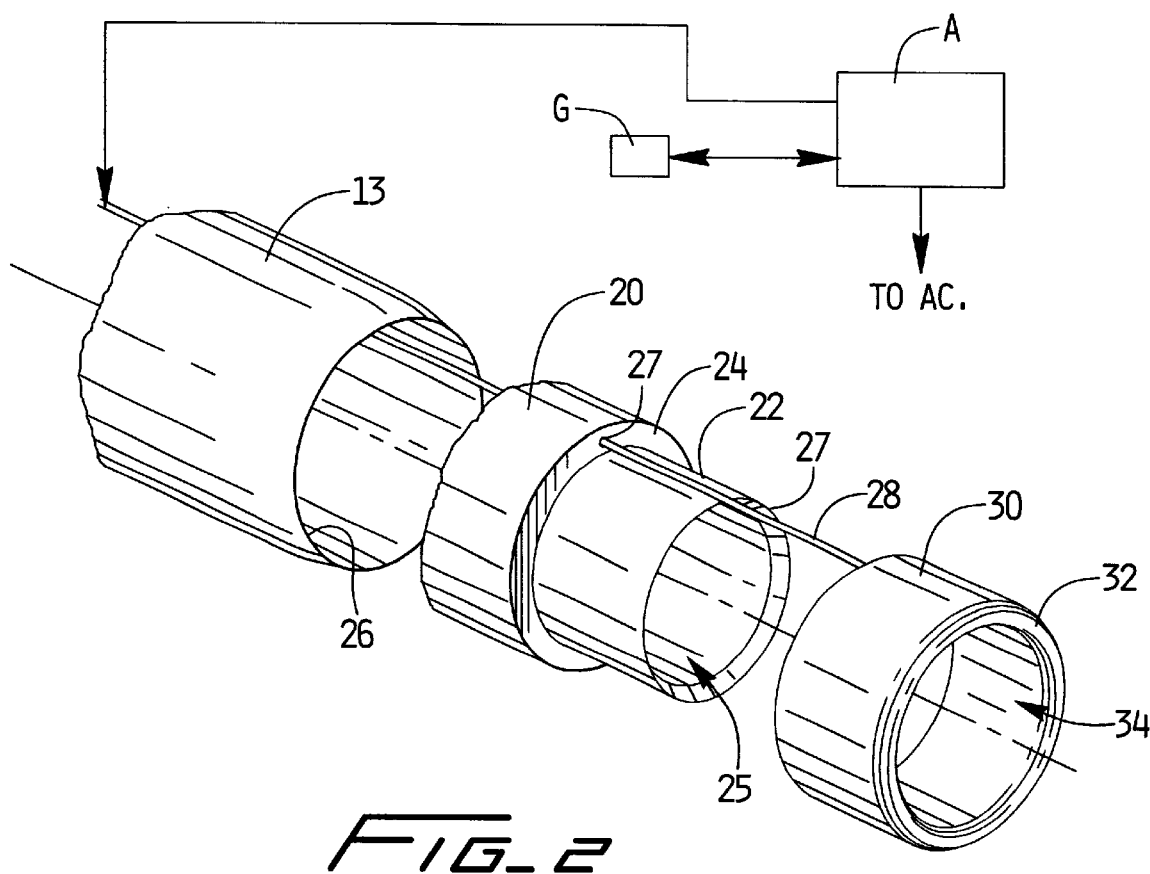
FIG_2
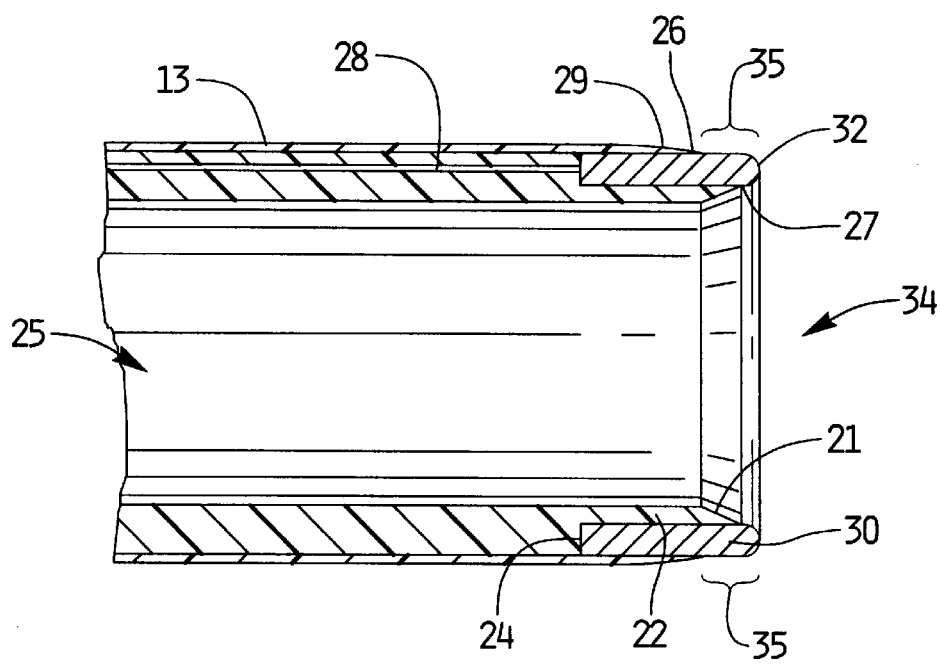
FIG_3

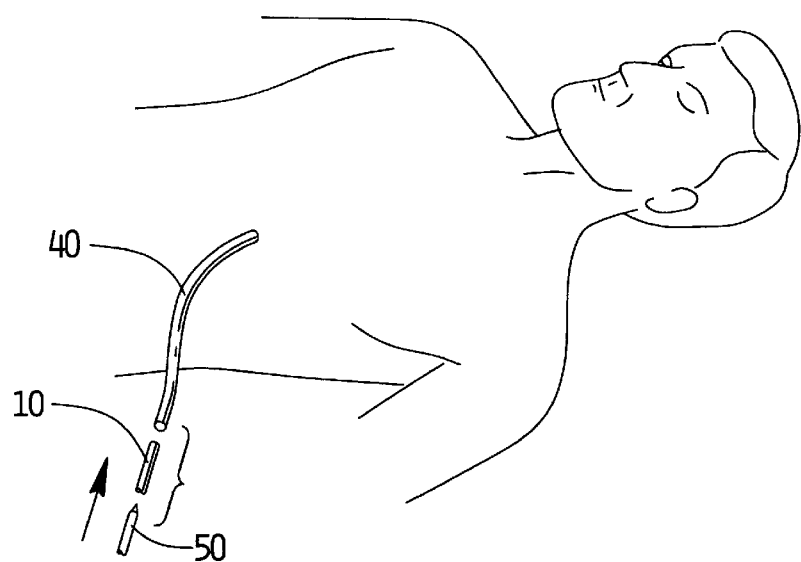
FIG_4
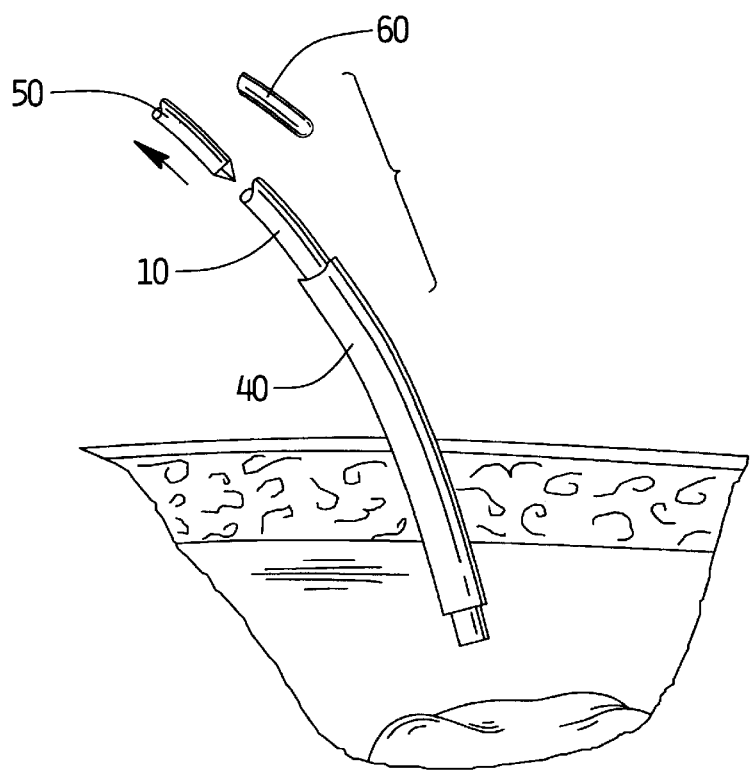
FIG_6A

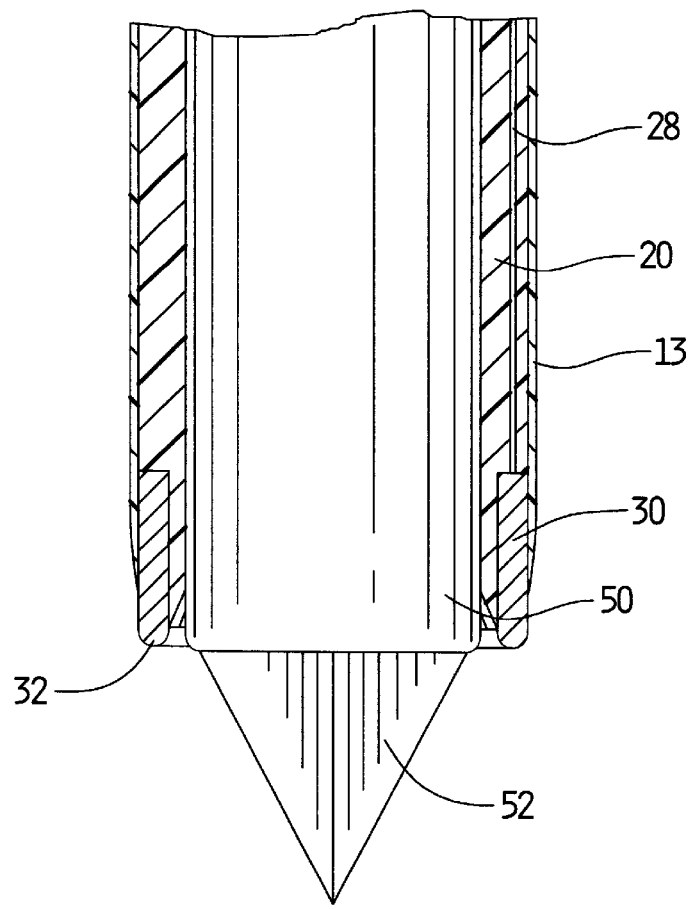
FIG_5
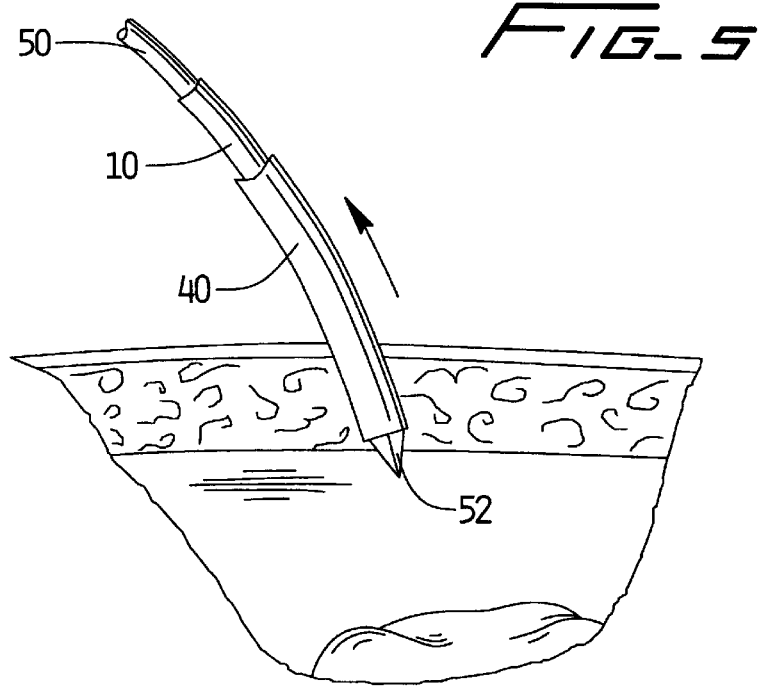
FIG_6

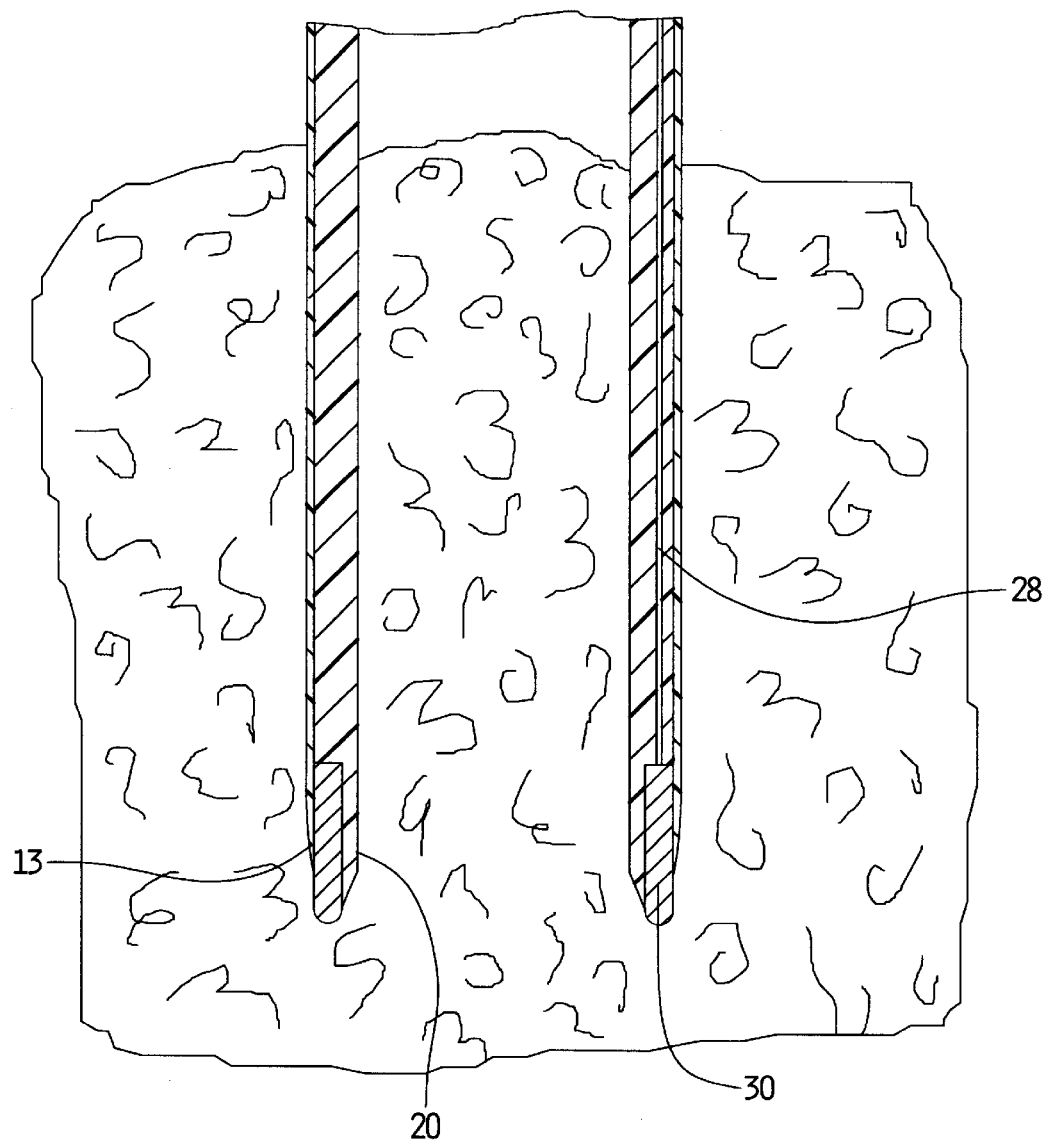

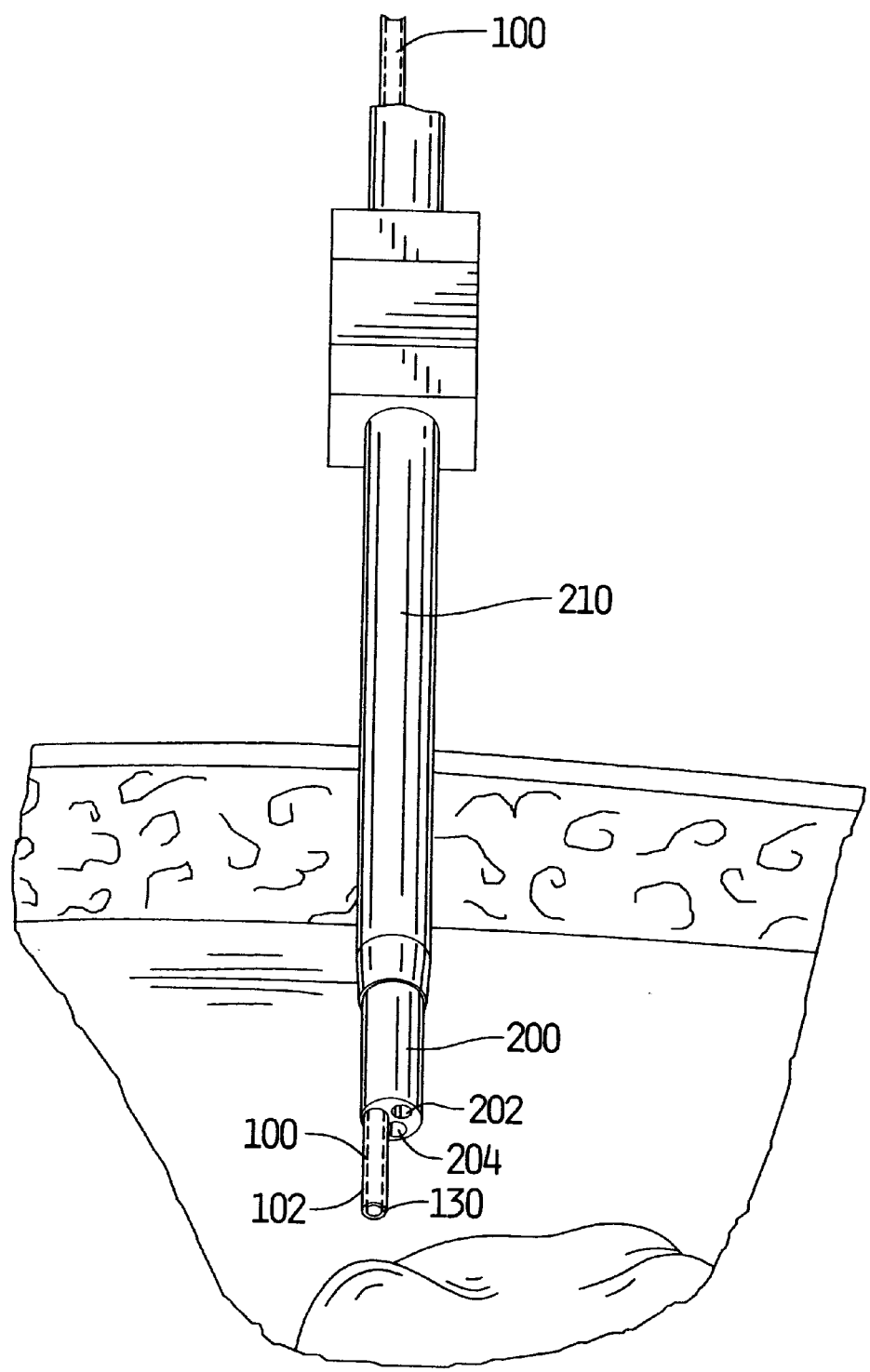
FIG_7

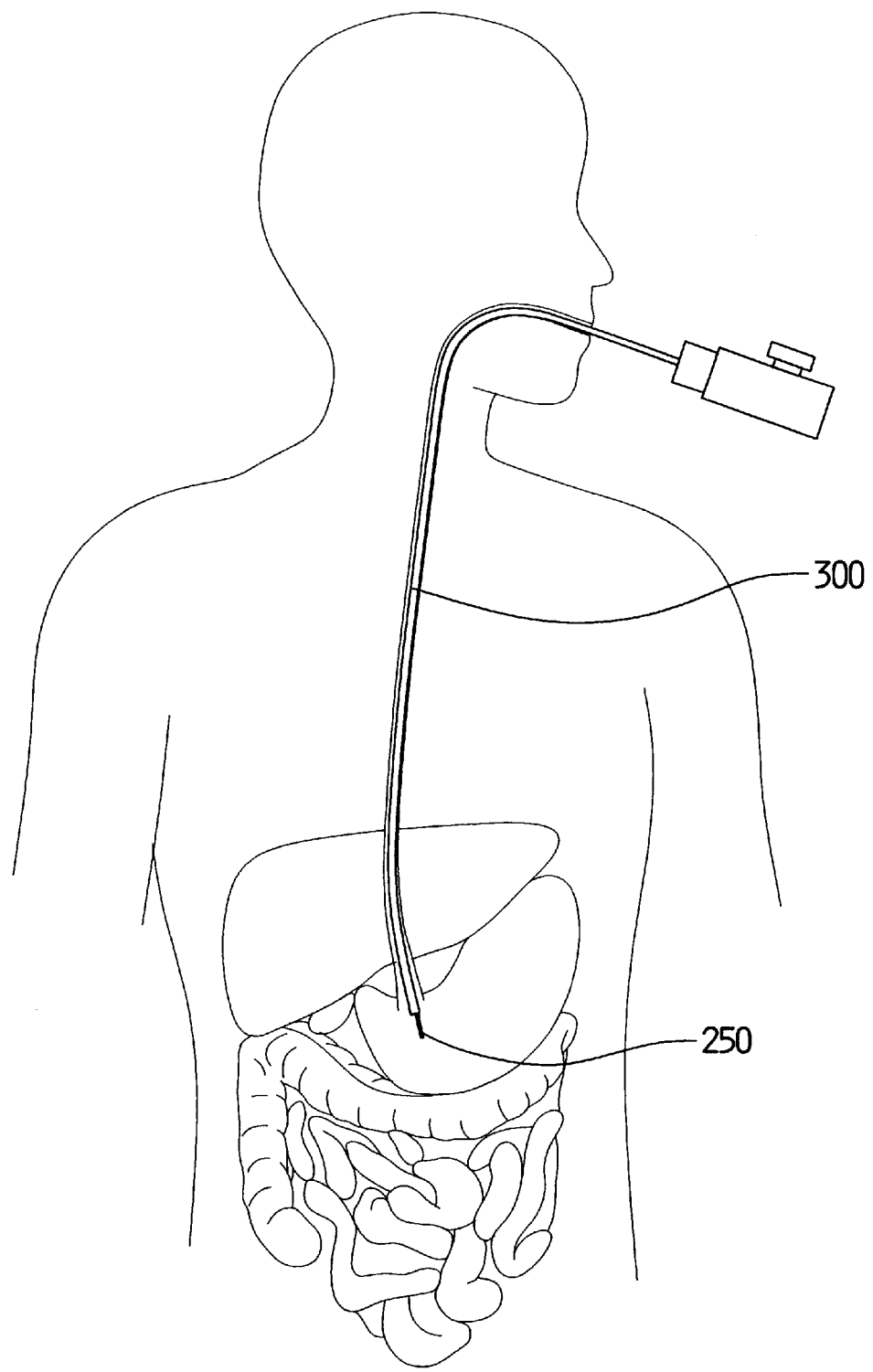
FIG_8

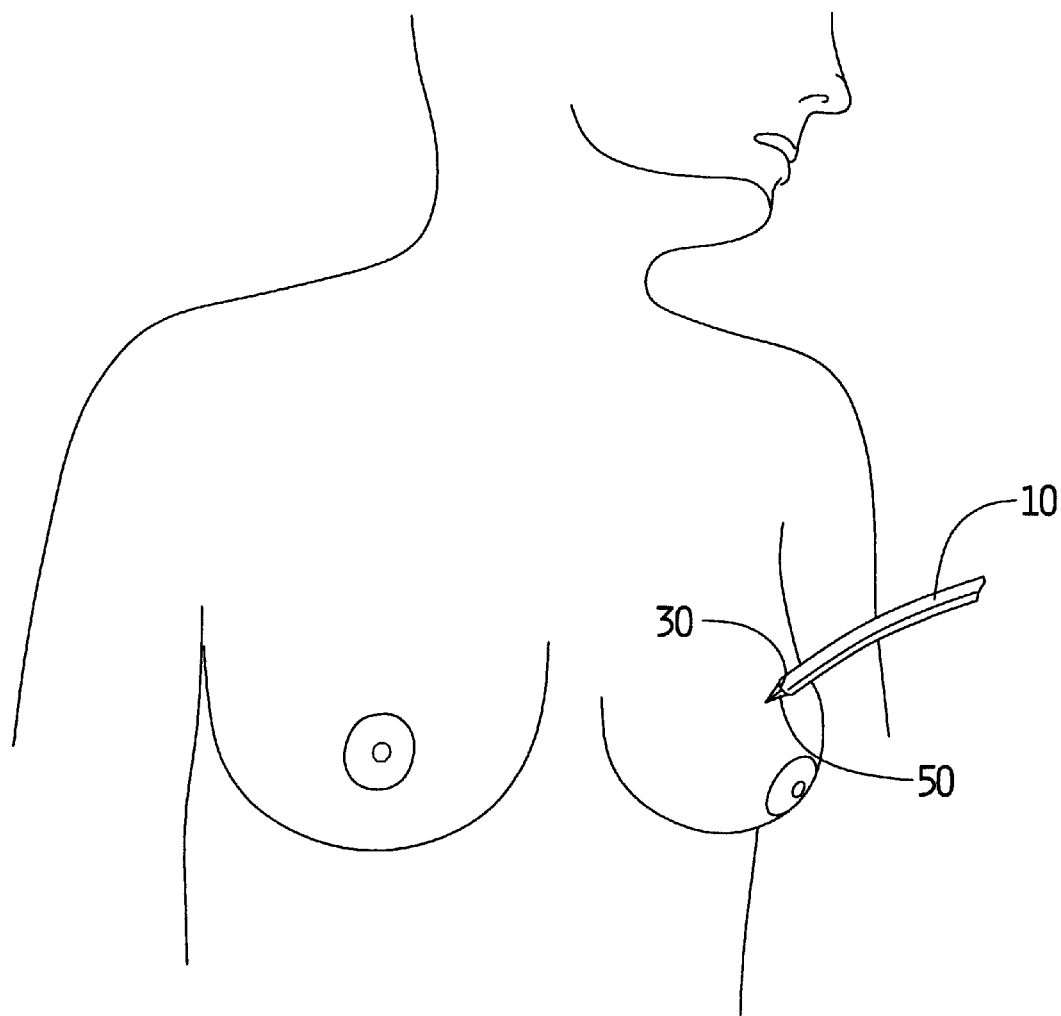
FIG_9

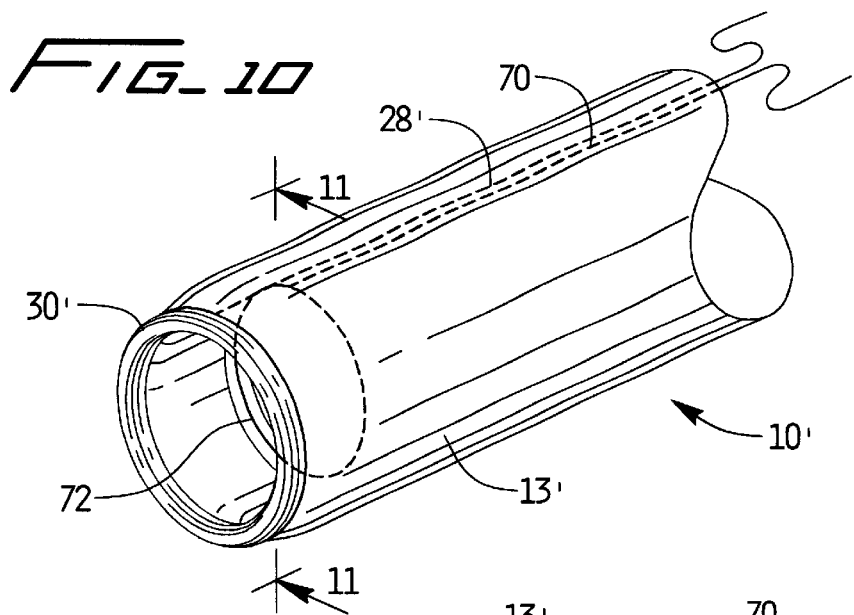
FIG_10
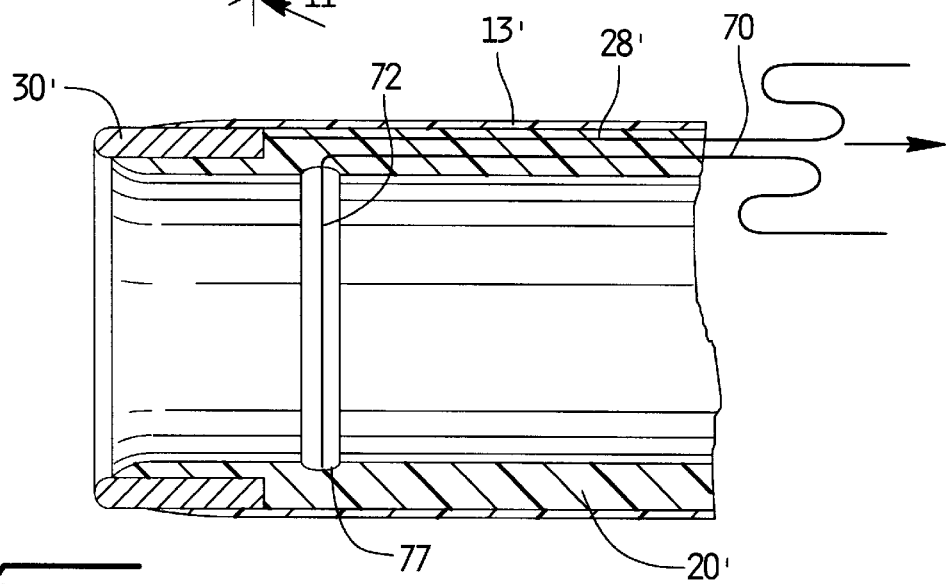
FIG_11
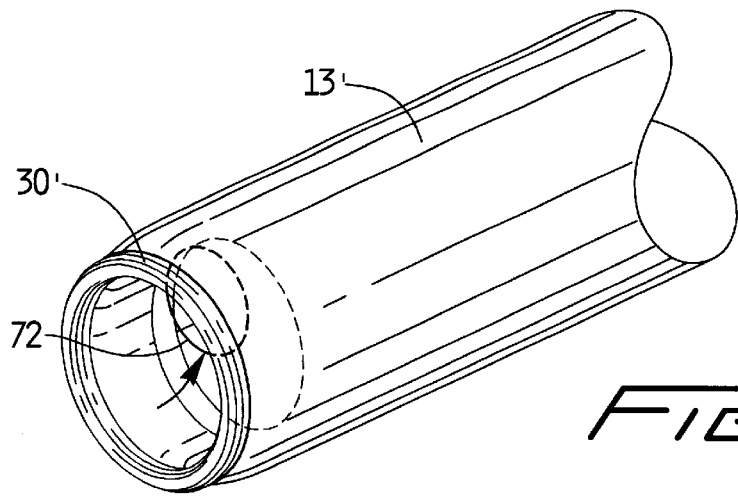
FIG_12

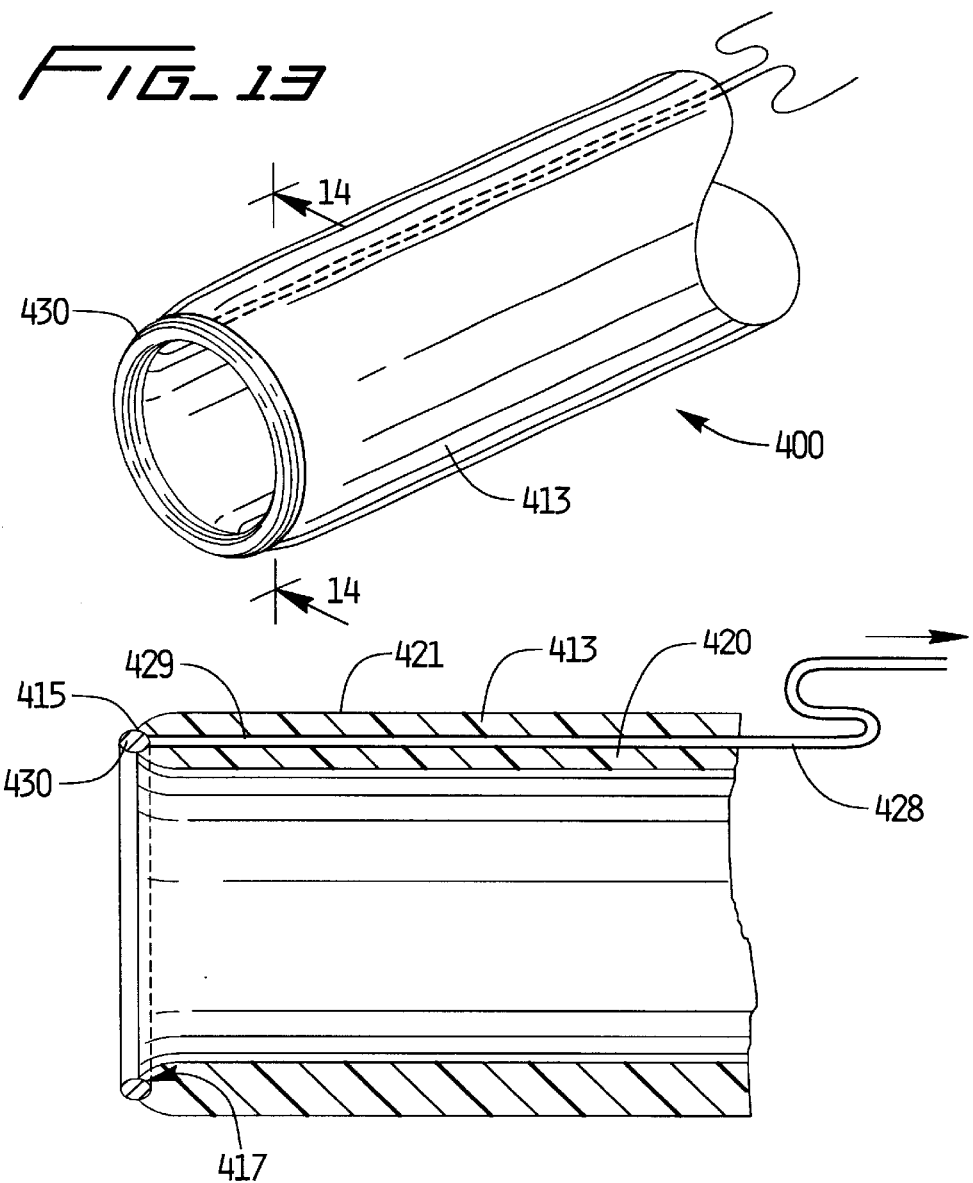
FIG_13
FIG_14
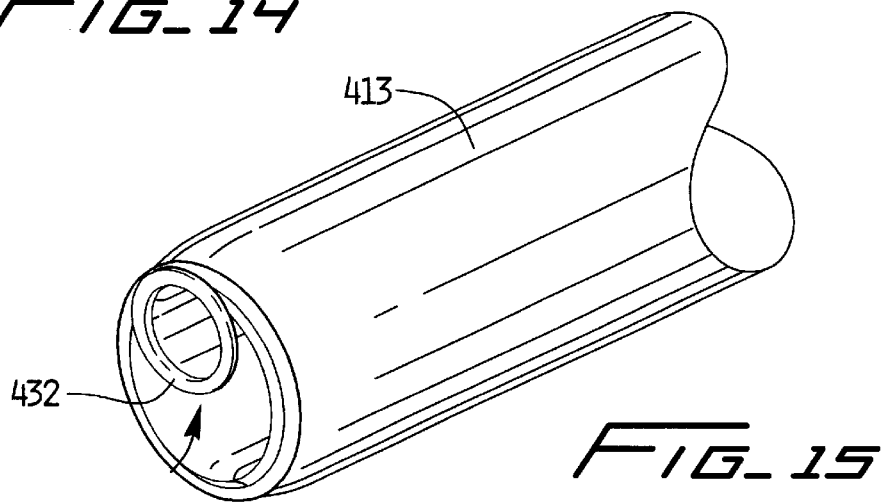
FIG_15

TISSUE BIOPSY APPARATUS WITH COLLAPSIBLE CUTTER

BACKGROUND

1. Technical Field

This application relates to a surgical apparatus and more particularly to a surgical biopsy apparatus for resecting and removing tissue through the apparatus.

2. Background of Related Art

Biopsy is the excision of a small section of tissue from a patient for diagnosis of malignancy or other diseases. For cancerous tissue and many other types of diseases, early diagnosis and tissue removal is critical since early detection increases the chances of successful treatment and survival.

Numerous devices are currently available for performing biopsies of tissue, such as breast tissue or liver tissue. These devices function to dissect a portion of the tissue and remove it from the body for pathology to determine whether the tissue is malignant.

The most invasive procedure is referred to as open excisional biopsy. In this procedure, large tissue samples are surgically removed through a large incision, requiring long patient recovery times, risking disfigurement, e.g. of the breast in breast biopsy, and resulting in increased pain, scarring and morbidity.

In an attempt to overcome the disadvantages of open surgery, more minimally invasive instruments have been developed. One minimally invasive approach utilizes a percutaneous instrument referred to as a fine needle biopsy instrument. In this instrument, a needle and syringe are inserted directly through the tissue, into the target tissue, e.g. the lump, to remove sample cells for pathology. For a breast biopsy, the instrument is inserted directly into the breast; for liver biopsy the instrument is inserted directly through the abdomen. One disadvantage of this technique is that numerous cell samples are required to be taken from the tissue to obtain a sufficient mass for testing, thereby requiring numerous needle sticks, increasing the time required for the procedure, and possible requiring re-localization by imaging of the lesion. Another disadvantage is that careful locational tracking of the tissue cells, which is required for accurate analysis, can be compromised. Also, with these devices there is a greater potential for false negatives due to the small sized specimens being removed without removal of sufficient surrounding areas of healthy tissue for comparison. Hemostasis during a biopsy is also an issue.

Another type of minimally invasive device is referred to as core needle biopsy. This device has a spring actuated cutter and removes a larger specimen than the fine needle biopsy instruments. The specimen is suctioned into a side window in the needle and then back through the proximal end of the needle. Although larger than fine needle biopsy instruments, these needles are still relatively small, e.g. 2 mm in diameter. Since typically removal of between five and twenty tissue cores of 2 mm in diameter and 20 mm in length is required for accurate pathology, five to twenty needle sticks into the patient of this 2 mm diameter needle is required. These devices also have the disadvantage that the spring force cutting action may displace malignant cells into the adjacent normal tissue or into the track along the path of entry. Thus, as the needle comes out, cancerous tissue can potentially be withdrawn. Also, the amount of false negatives can be high because of inadequate removal of surrounding healthy tissue. Like fine needle biopsy, success and accuracy of the procedure is skill dependent because the device must be maneuvered to various positions and these different positions accurately tracked.

Some percutaneous devices enable multiple specimens to be removed with a single needle stick. The specimens are removed from the proximal end of the needle by a vacuum. However, the device has a window formed in the sidewall to receive the tissue for resection by a cutter. Since only the tissue received within this lateral window is cut, the amount of tissue that can be removed and cut is limited. Therefore, the device must be rotated and maneuvered so different tissue sections can enter the window and be resected. This manipulation is not only time consuming and skill dependent, but detracts from the accuracy of tracking the tissue, thereby reducing the diagnostic accuracy.

To remove larger specimens of tissue utilizing this lateral window approach, the device would have to be made significantly larger. However, if made too large, then the procedure becomes more invasive and starts to resemble an open surgical procedure with the attendant disadvantages enumerated above. The larger instrument can cause additional bleeding because of the large incision and requires closure of a larger incision, thereby increasing scarring, lengthening patient recovery time, and adding to the cost, time and complexity of the procedure. Additionally, if the needle is too large than a large amount of tissue will be removed in the path from the skin surface entry point to the interior of the target tissue where the lesion is located. If pathology indicates the lesion is benign, then a large tissue mass would have been unnecessarily removed, resulting in more pain, a larger scar, and possible disfigurement. The disfigurement issue is more pronounced with procedures such as breast biopsy.

It would therefore be advantageous to provide a surgical biopsy device which is easy to use, reduces surgical procedure time, reduces bleeding and can minimally invasively remove large tissue samples sufficiently intact to improve the accuracy of pathology.

SUMMARY

The present invention overcomes the disadvantages and deficiencies of the prior art by providing a surgical apparatus for removing a portion of tissue comprising an elongated body having a distal edge, a collapsible cutting member mounted to the elongated body, having an opening therethrough, and extending distally of the distal edge of the elongated body. The cutting member has a closed loop conductive surface and is movable from a first loop configuration to a second smaller loop configuration. An exposed conductive distal edge of the cutting member forms an electrosurgical cutting surface for applying electrical energy to tissue. The cutting member resects a tubular region of tissue as the apparatus is advanced through tissue and the resected tissue extends through an opening in the cutting member for containment within the elongated body. The cutting member is movable to the second loop configuration to further sever the tissue.

The elongated body is preferably flexible and preferably comprises an inner tube and an outer tube wherein the cut tissue is stored in an interior lumen of the inner tube. The cutting member is preferably electrically connected to an RF generator to apply RF energy to the tissue.

In one embodiment, the elongated body of the apparatus is dimensioned for insertion through a working channel of an endoscope. In other embodiments, the elongated body is inserted laparascopically through a trocar, intraluminally through a catheter, or directly through the skin (percutaneously).

An obturator can be positioned within the elongated body which is extendable distally from the elongated body past the distal edge of the cutting member to penetrate tissue. The obturator is preferably spring biased to a protected retracted position such that a sharp tip of the obturator is positioned proximally of the distal edge of the cutting member.

The present invention also provides a surgical tissue biopsy system comprising an endoscope having a channel formed therein for receiving a surgical instrument, and a tissue biopsy apparatus insertable through the channel of the endoscope. The biopsy apparatus is connectable to a generator for supplying RF energy and has a collapsible cutting member mounted at a distal end thereof. The cutting member has a distally exposed conductive cutting surface for cutting tissue as the apparatus is advanced and the cutting member is energized to apply radiofrequency energy to the tissue. The cutting member is collapsible to a smaller configuration to farther sever tissue.

The cutting member preferably forms a substantially circular loop having a distal edge protruding from an elongated body member of the apparatus.

The present invention also provides a method of taking a tissue biopsy comprising:

providing an apparatus having an elongated member and a collapsible cutting member forming a cutting loop with a distally exposed conductive cutting surface fixedly mounted to the elongated member and extending past the elongated member;

introducing the apparatus into the body;

applying radiofrequency energy to the cutting member in a first loop configuration;

advancing the apparatus so the exposed surface contacts and severs the target tissue and enables the severed tissue to be captured within the interior of the elongated member; and collapsing the cutting member to a second smaller loop configuration.

The step of collapsing the cutting member preferably comprises pulling the member proximally to reduce the size of the cutting loop.

In one embodiment, the method further comprises the step of inserting the apparatus through a working channel in an endoscope. In this embodiment, the apparatus can be introduced transjugularly or transanally into the body. In another embodiment, the step of introducing the apparatus into the body comprises the step of introducing the apparatus percutaneously into the body.

The method of introducing the apparatus into the body may also include the step of distally advancing an obturator to penetrate tissue. The method may also further comprise the step of removing the tissue from the interior of the elongated member after the procedure by advancing the obturator within the elongated member to eject the tissue.

In one embodiment, the step of introducing the apparatus into the body comprises the step of introducing the apparatus into breast tissue for severing and removing a lesion in the breast. In another embodiment, the step of introducing the apparatus comprises the step of advancing the apparatus through the esophagus and stomach wall into the liver or kidney.

BRIEF DESCRIPTION OF THE DRAWINGS

Preferred embodiment(s) of the present disclosure are described herein with reference to the drawings wherein:

FIG. 1 is a perspective view of a first embodiment of the flexible tissue biopsy apparatus of the present invention;

FIG. 1A is an enlarged perspective view of the distal portion of the biopsy apparatus of FIG. 1;

FIG. 2 is an exploded perspective view of the distal portion of the biopsy apparatus of FIG. 1 and further schematically showing the electrosurgical system for energizing the apparatus;

FIG. 3 is a cross-sectional view taken along lines 3—3 of FIG. 1A;

FIG. 4 is a perspective view of one insertion method of the biopsy apparatus of FIG. 1 wherein it is introduced laparascopically (through the abdominal wall), the Figure showing the biopsy apparatus and the obturator outside the flexible introducer sheath;

FIG. 5 is an enlarged cross-sectional view of a distal portion of the biopsy apparatus of FIG. 1 showing the obturator positioned within the apparatus and in an extended position to penetrate tissue;

FIG. 6 is a side view showing the apparatus of FIG. 1 with the obturator positioned within the biopsy apparatus inside the introducer sheath and in the extended position to penetrate into the abdominal cavity;

FIG. 6A is view similar to FIG. 6 except showing the obturator being withdrawn from the biopsy apparatus and the biopsy apparatus advanced distally from the flexible introducer sheath for resection of tissue from the liver;

FIG. 6B is a cross-sectional view of a distal region of the biopsy apparatus of FIG. 1 showing the apparatus advanced through tissue for removal of a tubular tissue section and containment of the tissue section within the lumen of the apparatus;

FIG. 7 is a perspective view of an alternate insertion method of the tissue biopsy apparatus of the present invention wherein the biopsy apparatus is inserted through a working channel of an endoscope which is shown penetrating the abdominal wall;

FIG. 8 is a side view of another insertion method of the tissue biopsy apparatus of the present invention wherein the apparatus is inserted transjugularly into the stomach through a working channel of an endoscope;

FIG. 9 is a perspective view of another application of the tissue biopsy apparatus of the present invention shown being inserted percutaneously into breast tissue with the obturator in the extended position to penetrate tissue;

FIG. 10 is a perspective view of the distal portion of an alternate embodiment of the tissue biopsy apparatus of the present invention having a cutting wire;

FIG. 11 is a cross-sectional view taken along lines 11—11 of FIG. 10;

FIG. 12 is a perspective view similar to FIG. 10 except showing the cutting wire loop being closed to sever tissue;

FIG. 13 is a perspective view of the distal portion of another alternate embodiment of the tissue biopsy apparatus of the present invention having a collapsible cutting ring;

FIG. 14 is a cross-sectional view taken along lines 14—14 of FIG. 13; and

FIG. 15 is a perspective view similar to FIG. 13 except showing the collapsible ring being closed to sever tissue.

DETAILED DESCRIPTION OF PREFERRED EMBODIMENTS

Referring now in detail to the drawings where like reference numerals identify similar or like components throughout the several views, FIG. 1 illustrates a first embodiment of the tissue biopsy apparatus of the present invention. The tissue biopsy apparatus is designed to resect tissue by application of radiofrequency (RF) energy and store the resected tissue section intact in a lumen of the apparatus. The apparatus 10 achieves this by a distally positioned stationary cutting ring 30 which resects tissue as the apparatus is advanced through tissue, progressively removing a continuous cylindrical section of tissue. The tissue sample can then be removed from the lumen and sent to pathology, with the continuous intact specimen increasing the accuracy of the testing and diagnosis of the tissue for malignancy or other diseases. The alternate embodiment depicted in FIG. 13 utilizes a collapsible cutting wire loop instead of the fixed cutting ring to resect a cylindrical tissue section in a similar fashion.

The apparatus 10 with the RF cutting ring has application in laparascopic approaches, endoscopic approaches both transanally and transjugularly such as through a bronchoscope, percutaneous approaches directly through the skin, and intraluminal approaches where it can penetrate the vessel wall from the inside to access an organ or other target tissue. Several of these approaches are illustrated in the drawings and described below.

Additionally, it may be desirable that the cutting ring be energized before the cutting ring is in contact with the tissue to be sampled. This facilitates cutting as it can prevent the tissue from potentially initially sinking the current. Therefore, a catheter or sheath can be provided in which the biopsy apparatus is removably positioned so that the power can be turned on to energize the apparatus while the cutting ring is shielded (retracted) within the catheter (sheath), followed by advancement into the target tissue. This is also discussed in more detail below.

The tissue biopsy apparatus of the present invention can be flexible to facilitate manipulation and navigation through the patient's body, or alternatively can be rigid if being used, for example, in certain laparascopic approaches.

Turning now to the details of the apparatus and with particular reference to FIGS. 1–3, biopsy apparatus 10 has a flexible elongated body 12 composed of a hollow outer sleeve 13 and a hollow inner tube 20 fixedly mounted therein. Positioned at the proximal portion of apparatus 10, extending proximally of elongated tubular body 12, is a handle grip 15 for grasping by the surgeon. Fixedly positioned at the distal end portion 14 of apparatus 10 is cutting ring 30 which forms a stationary electrode for transfer of RF energy to the tissue which when energized, enables the apparatus to advance through tissue, resecting the tissue section as it is advanced and capturing the resected tissue within the lumen 25 of inner tube 20. Distal edge 26 of outer sleeve 13 is preferably tapered along surface 29, forming a beveled edge to facilitate passage through tissue. The distal end of inner tube 20 can also be beveled at surface 21 as shown.

Inner tube 20 has a reduced diameter portion (waist) 22 forming a shoulder 24. Cutting ring 30 is fixedly mounted on the outer surface of waist 22 in abutment with shoulder 24 by compression fitting, insert molding, or other attachment means. The cutting ring 30, as shown, is cylindrically shaped in a closed loop and is hollow forming an opening 34 for resected tissue. The cutting ring 30 has a distal edge 32 that extends slightly distal of the distal edge 26 of outer sleeve 13 and the distal edge 27 of inner tube 20. Thus, only the distal edge 32 and the surface slightly proximal of the edge 32, designated as area 35, is exposed to the tissue. Consequently, when RF power is applied, only the annular exposed surface 35 and annular edge 32 of the cutting ring 30 applies RF energy to cut and cauterize the tissue.

A conductive wire 28 extends from cutting ring 30 through axial channel 26 formed throughout the length of inner tube 20, extending proximally from the apparatus for connection to an electrosurgical generator. That is, wire 28 electrically connects cutting ring 30 to RF generator box "A", shown schematically, which is plugged into an AC power supply, or alternatively is battery powered. Conventional ground plate G is also shown schematically and is electrically connected to generator A and functions as a return electrode as in conventional monopolar systems.

As explained above, the distal edge 32 of cutting ring 30 protrudes distally from the distal edges 26, 27 of outer sleeve 13 and inner tube 20, respectively, so it is exposed to body tissue. As the apparatus 10 is energized by the RF generator and advanced through tissue, the exposed edge 32 and exposed adjacent surface 35 cut and cauterize the tissue, forming a cylindrical resected tissue section (circular in cross section). As the cutting ring 30 advances, the resected solid tubular section passes through opening 34 in cutting ring 30 and through lumen 25 of inner tube 20 where it is stored therein for subsequent removal for pathology.

To ensure energy flow through wire 28 to cutting ring 20, inner tube 20 is composed of a non-conductive material. This insulates wire 28. Additionally, outer sleeve 13 is composed of a non-conductive material, although alternatively, it can be composed of a conductive material with the portions of the sleeve in contact with and adjacent cutting ring 30 composed of a non-conductive material or a non-conductive coating. If inner tube 20 is composed of conductive material, wire 28 is contained in an insulated sleeve and the portions of the inner tube 20 in contact with cutting ring 30 are electrically non-conductive.

It should be appreciated that the apparatus 10 can be inserted with the aid of an obturator, such as obturator 50 of FIGS. 5 and 6. The obturator is positioned within the lumen 25 of inner tube 20 and has a sharp penetrating tip such as a trocar tip 52 shown in FIG. 6. Alternatively, the obturator can have a blunt tip as in obturator 60 of FIG. 6A. Obturator 50 is preferably spring biased proximally and is thumb actuated by the user. The user would press the thumb button (not shown) at the proximal end of the obturator, forcing the obturator distally from the inner tube 20 to expose the penetrating tip 52 from its retracted position where it is shielded within the inner tube 20 to an extended position where the penetrating tip 52 extends distally from the inner tube 20 and extends past the distal edge 32 of the cutting ring 30. With the obturator in this position, the apparatus 10 is forced through tissue to the target site. Once at the target site, the thumb button is released, allowing the obturator to return to its retracted position, enabling the penetrating tip 52 to retract within the confines of inner tube 20. This is further described below.

Turning now to the method of use of the apparatus, the apparatus of the present invention can be inserted in a variety or ways to treat different regions of the body. For example, the apparatus can be inserted percutaneously, i.e. directly through the skin into the target tissue. The apparatus can also be inserted laparascopically where it is inserted through a trocar extending through the abdominal wall. Further, the apparatus can be inserted endoscopically, through a working channel of an endoscope that is inserted into the patient either transanally or transjugularly. Still further, the apparatus can be inserted transluminally through a vessel.

An example of the percutaneous approach is illustrated in FIGS. 4–6B. An incision is made through the stomach and a flexible introducer sheath 40 along with the apparatus 10 and obturator 50 are inserted therethrough, penetrating the stomach wall into the abdominal cavity as shown in FIG. 4. The cavity can be insuffflated in certain applications. FIG. 4 shows the sheath 40, apparatus 10 and obturator 50 separated for convenience, although they would be inserted as a unit in this embodiment.

More specifically, obturator 50 has a penetrating tip which is spring biased to the retracted position. Thus the tip 52 is normally shielded within the obturator cannula. For insertion, the obturator 50, which is positioned within the internal lumen 25 of inner tube 20, is actuated to advance the tip 52 out of the cannula and distally of the inner tube 20 and introducer sheath 40. This actuation can be achieved by pressing a thumb button on the proximal end or by other conventional means. With the tip 52 in the exposed position, the sheath 40 and apparatus 10 therein can be advanced through the tissue as shown in FIGS. 6 and 6A. Once the sheath is in position, the surgeon releases the thumb button, causing the tip 52 to automatically retract to a shielded position, and the obturator is withdrawn. Alternatively, the apparatus and obturator can be advanced together with respect to the introducer sheath 40. That is, the sheath would remain in its position, and the tip of the obturator exposed to advance through additional tissue to deliver the apparatus 10 to the target tissue. Once at the target tissue, the obturator would be removed from the apparatus and the introducer sheath 40.

Once the obturator 50 is withdrawn, the apparatus 10 is then energized to apply RF energy to cutting ring 30 via connecting wire 28 to resect the tissue. The RF energy both cuts and coagulates the tissue, and cores through the tissue as the apparatus 10 and cutting ring 30 are advanced, minimizing peripheral burn. As can be appreciated, the cutting ring 30 resects a tubular section of tissue, having a cross-sectional dimension substantially corresponding to the internal diameter of the cutting ring 30. Either small bites of tissue can be taken, with the power repeatedly turned on and off, or the power can be left on, taking a continuous elongated tubular section of tissue. The resected tissue is contained within the internal lumen 25 of inner tube 20, with the cross sectional dimension substantially corresponding to the diameter of the lumen 25. The apparatus is then removed from the patient. If desired, the obturator can be reinserted to force the tissue sample(s) distally out of lumen 25 of inner tube 20 for testing of the sample.

Note that FIG. 6A shows as an alternative a blunt tipped obturator 60 which would be inserted in the same manner as obturator 50, except it would bluntly dissect the tissue during penetration. It should be appreciated that the obturator can be biased in a variety of ways and can be actuated by mechanisms other than a thumb button. The obturator can also be configured so that the apparatus is biased with respect to the obturator. Also, the obturator can alternatively be automatically retractable within the inner tube after initial tissue penetration.

The obturator can be used at the end of the procedure to eject the tissue sample from the lumen in the inner tube. In this version, the obturator would remain withdrawn inside the apparatus and the user would then press the thumb button so the distal end of the obturator contacts the tissue sample and forces it from inner tube 20. Suction can also be used to remove the sample when the instrument is inside or outside the patient.

In an alternate insertion method, the introducer sheath 40 can be in the form of a cannula portion of a conventional trocar which has a removable obturator (not shown) with a penetrating tip initially inserted with the cannula to penetrate tissue, and then removed, leaving the cannula (sheath) in place. In this embodiment, the introducer sheath 40 is placed first, and then obturator 50 and apparatus 10 are introduced as a unit through the introducer sheath 40. The obturator tip 52 is then extendable from the inner tube 20 to enable the apparatus to be advanced to the desired tissue site.

An alternative embodiment of the apparatus of the present invention is depicted in FIG. 7. Apparatus 100 is dimensioned for insertion through an endoscope channel which is dimensioned to receive a surgical instrument therethrough and is commonly referred to as a working channel. Endoscope 200 can be placed through a trocar 210, which is preferably flexible, for endoscopic or laparascopic surgical applications, such as for laparascopic liver biopsy. Optics 202, 204 illuminate the surgical site and provide images for viewing the site. The apparatus 100 as shown is inserted through the skin and stomach wall to access the liver. RF energy is applied to the distal cutting ring 130 extending distally from the outer sleeve and inner tube in the same manner as described above. The resected tissue from the liver is stored within the inner tube and subsequently removed for pathology. The endoscope utilized can be flexible or alternatively can be a rigid endoscope.

A sheath 102 can optionally be provided, surrounding at least a distal portion of the apparatus 100 and also positioned within the working channel of the endoscope 200. The apparatus 100 and sheath 102 can be extended through the working channel distally of the endoscope with the distal cutting edge remaining shielded within the sheath 102. The cutting ring 130 can then be energized within the sheath 102, prior to contact with tissue, and then advanced from sheath 102 into tissue once energized.

An obturator can be removably positioned within the apparatus. In this way, the apparatus and obturator can be advanced distally of the endoscope, and the obturator extended to penetrate tissue to advance the cutting ring to the desired site.

FIG. 8 illustrates another application of the apparatus of the present invention. The flexible apparatus is inserted transjugularly through a conventional flexible endoscope 300. As shown, the apparatus 250 extends through a working channel of the endoscope, which extends through the patient's mouth and throat, down through the esophagus and stomach wall and into the bowel to access the liver or the kidney. Apparatus 250 contains an identical annular cutting ring as apparatus 10 and is energized and advanced in the same manner as described above. A sheath similar to the aforedescribed sheath 102 could optionally be utilized. The apparatus can also include an obturator which could be used to enable the apparatus to penetrate the stomach wall to access the desired tissue, e.g. the liver.

The obturator could also be used if the apparatus is used intraluminally in that obturator would penetrate the vessel wall to allow the cutting ring to access and energize the tissue outside the vessel. Alternatively, the RF energy can be used to penetrate the vessel wall.

FIG. 9 illustrates removal of breast tissue utilizing the apparatus of FIG. 1. Apparatus 10 is inserted percutaneously with the aid of obturator 50 through the breast tissue to access the lesion. RF energy is applied to the cutting ring 30 to resect a portion of the lesion and contain it within the internal lumen for withdrawal and pathology in the manner described above.

FIG. 10 illustrates an alternate tissue biopsy apparatus of the present invention. Apparatus 10' is identical to apparatus 10 described above except for the provision of a cutting wire 70 and groove 77 formed in the inner tube 20'. Common parts between apparatus 10' and apparatus 10 are identified with the same numerals, except for the prime designation for apparatus 10'. Cutting wire 70 has a loop 72 which is seated within groove 77 and extends through a channel in the inner tube 20', with the proximal end exiting the proximal end of the apparatus 10'. After the tissue section has been cored by cutting ring 30' as the apparatus is advanced through tissue in the manner described above, the tissue section can be severed by pulling wire 70 proximally in the direction of the arrow (FIG. 11) to thereby close the loop (FIG. 12) around the tissue. FIG. 12 shows the loop 72 in the open and in the partially closed position. As shown, wire loop 72 is preferably positioned proximal of cutting ring 30'. Loop 72 can have a cutting edge to mechanically sever the tissue or alternately be connected to a RF source to electrically sever the tissue. Apparatus 10' can be used in the same surgical applications as described with respect to apparatus 10.

FIGS. 13–15 illustrate an alternate embodiment of the tissue biopsy apparatus of the present invention which instead of a stationary cutting ring, utilizes a collapsible cutting wire. Apparatus 400 has a tube or sleeve 413, preferably flexible, having an annular groove 417 formed at a distal end for receiving the cutting member 430. (Only the distal end of the apparatus is shown.) Alternatively, an outer and inner tube could be utilized, with the cutting member mounted therebetween.

Cutting member 430 forms an electrode for transfer of RF energy to tissue and is positioned at the distalmost end of the apparatus, extending past the distalmost edge 415 of sleeve 413 similar to the way ring 30 extends past the distal edges of sleeve 13 and inner tube 20 of apparatus 10 of FIG. 1. However, unlike ring 30, cutting member 430 is in the form of a movable cutting wire with a looped end seated within groove 417. Cutting member 430 is movable between an expanded position wherein the loop 432 forms a first loop having a first diameter substantially corresponding to the diameter of the sleeve 413 (see FIGS. 13 and 14) and a collapsed position wherein the loop 432 forms a second loop having a second diameter smaller than the first diameter.

Conductive wire portion 428 is preferably integral with loop 432 and electrically connects cutting loop 432 to a RF energy source to apply RF energy to the tissue. Portion 428 extends in the channel formed between wall portions 421 and 429, exiting the proximal end of the instrument.

The apparatus 400 is advanced with the loop in the enlarged position and RF energy is applied to the tissue via the loop to core through tissue in the manner described above with respect to apparatus 10 and 10'. After coring, the proximal portion of the cutting wire is pulled proximally in the direction of the arrow of FIG. 14, tightening the loop around the tissue (see the arrow in FIG. 15). This tension pulls loops 432 out of groove 417 and collapses loop 432 to sever the end of the tissue, thereby separating the tubular tissue section from the patient to fully capture it within the lumen of the tube 413. Thus, the RF energy applied through loop 432 resects the distal end of the tissue section.

Note that FIG. 15 shows the loop 432 in the partially collapsed position, it being understood that fuller closure would be required to sever the tissue. The wire loop can be energized before the loop is in contact with the tissue to be sampled by containment within a sheath as described above with respect to apparatus 10

Apparatus 400 can be used for the same surgical applications and the same methods of insertion as described herein with respect to apparatus 10.

As can be appreciated, the biopsy apparatus of the present invention can remove a relatively large area of tissue, and can remove a continuous solid cylindrical strip of tissue which is intact to improve the accuracy of pathology. The strip can be continuous if the RF energy is constantly applied during the resecting process, or, if RF energy is applied intermittently, could be a series of discrete adjacent cylindrical portions which also facilitates pathology.

The cutting ring (and wire loop) is preferably the same cross-sectional shape as the cross-sectional shape of the cannula, thereby conforming to its cross-sectional dimensions. Such preferred embodiment enables a tissue section to be severed substantially equal to the diameter of the cannula, thereby striking a balance between a larger incision if the cutting ring or loop exceeded the cannula diameter and a smaller tissue biopsied if the cutting ring or loop is smaller than the cannula. Obviously, however, although not necessarily optimal, a smaller or larger cutting ring or loop relative to the cannula could be utilized. Additionally, although the cutting ring or loop is shown as circular in cross-section, it is also contemplated that the cutting ring or loop could be oval or elliptical in cross-sectional shape to form a closed loop to encircle the tissue. Other shapes are also contemplated.

The apparatus of the present invention can be used for biopsy of different types of tissue, including but not limited to breast tissue, liver, pancreas, brain, polyps, kidneys and lymph nodes.

If not used with an endoscope, the apparatus can be used with various known imaging techniques such as tomographic, stereotactic and ultrasonic imaging.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical apparatus for removing a portion of tissue comprising an elongated body having a distal edge and a retaining groove, a collapsible cutting member having an opening therethrough, the collapsible cutting member mounted to the elongated body and captured within the retaining groove such that a distal surface of the cutting member extends distally of the distal edge of the elongated body so the distal surface is exposed to transmit electrical energy to tissue and a proximal surface is insulated, the cutting member having a closed loop conductive surface and movable from a first loop configuration to a second smaller loop configuration, the cutting member resecting a tubular region of tissue as the apparatus is advanced through tissue and the resected tissue extending through the opening in the cutting member for containment within the elongated body, and the cutting member movable out of the retaining groove to the second loop configuration to further sever the tissue.

2. The apparatus of claim 1, wherein the elongated body is flexible.

3. The apparatus of claim 1, wherein the cutting member is electrically connected to an RF generator to apply RF energy to the tissue.

4. The apparatus of claim 1, wherein the cutting member forms one of the electrodes of a monopolar system.

5. The apparatus of claim 1, wherein the elongated body comprises an inner tube and an outer tube, and the resected tissue is stored in an interior lumen of the inner tube.

6. The apparatus of claim 1, wherein the elongated body is dimensioned for insertion through a working channel of an endoscope.

7. The apparatus of claim 1, further comprising an obturator positioned within the elongated body and extendable distally from the elongated body to penetrate tissue, the obturator being extendable past the distal surface of the cutting member.

8. The apparatus of claim 7, wherein the obturator is spring biased to a protected retracted position such that a sharp tip of the obturator is positioned proximally of the distal surface of the cutting member.

9. A surgical tissue biopsy system comprising:
an endoscope having a channel formed therein dimensioned for receiving a surgical instrument; and
a tissue biopsy apparatus insertable through the channel of the endoscope, the biopsy apparatus connectable to a generator for supplying radiofrequency energy, the biopsy apparatus having a first transverse dimension, a retention groove and a collapsible cutting member mounted within the retention groove so as not to exceed the first dimension of the apparatus, the cutting member mounted at a distal end of the apparatus, wherein the cutting member has a distally exposed conductive cutting surface for cutting tissue as the apparatus is advanced and the cutting member is energized to apply radiofrequency energy to the tissue, the cutting member being displaced from the retaining groove and collapsible to a smaller configuration to further sever tissue.

10. The system of claim 9, wherein the cutting member forms a substantially circular loop.

11. The system of claim 10, further comprising a radiofrequency generator electrically connected to the tissue biopsy apparatus.

12. A method of taking a tissue biopsy comprising:
providing an apparatus having an elongated member, a fixed cutting ring and a collapsible cutting member forming a cutting loop positioned proximally of the fixed cutting ring, the fixed cutting ring having a distally exposed conductive cutting surface mounted to the elongated member and extending distally beyond the elongated member;
introducing the apparatus into the body;
applying radiofrequency energy to the fixed cutting ring;
advancing the apparatus so the exposed surface contacts and cores the target tissue and enables the cored tissue to be captured within an interior of the elongated member; and
thereafter collapsing the cutting loop of the cutting member to a second smaller loop configuration to sever the cored tissue.

13. The method of claim 12, wherein the step of introducing the apparatus into the body further comprises the step of inserting the apparatus through a working channel in an endoscope.

14. The method of claim 12, wherein the step of introducing the apparatus into the body comprises the step of introducing the apparatus transjugularly into the body.

15. The method of claim 12, wherein the step of introducing the apparatus into the body comprises the step of introducing the apparatus percutaneously into the body.

16. The method of claim 12, wherein the apparatus includes an obturator with a sharp tip positioned in the elongated member and the step of introducing the apparatus into the body includes the step of distally advancing the obturator to penetrate tissue.

17. The method of claim 16, further comprising the step of removing the tissue from the interior of the elongated member after the procedure by advancing the obturator within the elongated member to eject the tissue.

18. The method of claim 12, wherein the step of introducing the apparatus into the body comprises the step of introducing the apparatus into breast tissue for severing and removing a lesion in the breast.

19. The method of claim 12, wherein the step of introducing the apparatus into the body comprises the step of advancing the apparatus through the esophagus and stomach wall into the liver or kidney.

20. The apparatus of claim 12, wherein the step of collapsing the cutting loop further comprises the step of pulling the cutting member proximally to reduce the size of the cutting loop.

21. The method of claim 12, wherein the step of collapsing the cutting loop to sever tissue includes the step of displacing the cutting loop from a groove in the elongated member and applying RF energy to the cutting loop.

* * * * *